United States Patent
Charrier et al.

(10) Patent No.: US 9,533,959 B2
(45) Date of Patent: Jan. 3, 2017

(54) METHODS OF REGIOSELECTIVE SYNTHESIS OF 2,4-DISUBSTITUTED PYRIMIDINES

(71) Applicant: Vertex Pharmaceuticals Incorporated, Boston, MA (US)

(72) Inventors: Jean-Damien Charrier, Abingdon (GB); Michael Edward O'Donnell, Abingdon (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/043,717

(22) Filed: Feb. 15, 2016

(65) Prior Publication Data

US 2016/0159749 A1 Jun. 9, 2016

Related U.S. Application Data

(62) Division of application No. 14/506,921, filed on Oct. 6, 2014, now Pat. No. 9,296,727.

(60) Provisional application No. 61/887,570, filed on Oct. 7, 2013.

(51) Int. Cl.
| | | |
|---|---|---|
| C07D 239/34 | (2006.01) | |
| C07D 239/47 | (2006.01) | |
| C07D 403/14 | (2006.01) | |
| C07D 239/48 | (2006.01) | |
| C07D 401/14 | (2006.01) | |

(52) U.S. Cl.
CPC ........... *C07D 239/47* (2013.01); *C07D 239/34* (2013.01); *C07D 239/48* (2013.01); *C07D 401/14* (2013.01); *C07D 403/14* (2013.01)

(58) Field of Classification Search
CPC .................................................. C07D 239/34
USPC ........................................ 544/319, 320, 321
See application file for complete search history.

(56) References Cited

U.S. PATENT DOCUMENTS

| | | | |
|---|---|---|---|
| 4,349,552 A | 9/1982 | Takaya et al. | |
| 7,507,826 B2 | 3/2009 | Salituro et al. | |
| 7,767,816 B2 | 8/2010 | Farmer et al. | |
| 8,513,414 B2 | 8/2013 | Tanoury et al. | |
| 8,796,453 B2 | 8/2014 | Tanoury et al. | |
| 8,829,007 B2 | 9/2014 | Charifson et al. | |
| 8,946,425 B2 | 2/2015 | Tanoury et al. | |
| 9,051,319 B2 | 6/2015 | Charifson et al. | |
| 9,090,614 B2 | 7/2015 | Tanoury et al. | |
| 9,296,727 B2 | 3/2016 | Charrier et al. | |
| 9,345,708 B2 | 5/2016 | Charifson et al. | |
| 9,394,302 B2 | 7/2016 | Charifson et al. | |
| 2008/0242663 A1 | 10/2008 | Ashton et al. | |
| 2012/0171245 A1 | 7/2012 | Charifson et al. | |
| 2013/0102782 A1 | 4/2013 | Tanoury et al. | |
| 2013/0303764 A1 | 11/2013 | Tanoury et al. | |
| 2014/0094473 A1 | 4/2014 | Charifson et al. | |
| 2014/0142119 A1 | 5/2014 | Charifson et al. | |
| 2014/0296201 A1 | 10/2014 | Charifson et al. | |
| 2014/0309421 A1 | 10/2014 | Tanoury et al. | |
| 2015/0099875 A1 | 4/2015 | Charrier et al. | |
| 2015/0099884 A1 | 4/2015 | Tanoury et al. | |
| 2015/0152103 A1 | 6/2015 | Salituro et al. | |
| 2015/0191468 A1 | 7/2015 | Charifson et al. | |
| 2015/0284388 A1 | 10/2015 | Tanoury et al. | |
| 2016/0152614 A1 | 6/2016 | Charifson et al. | |

FOREIGN PATENT DOCUMENTS

| | | |
|---|---|---|
| WO | WO 99/50250 | * 10/1999 |
| WO | 2005/033072 | 4/2005 |
| WO | 2005/095400 | 10/2005 |
| WO | 2007/084557 | 7/2007 |
| WO | 2010/148197 | 12/2010 |
| WO | 2013/006634 | 1/2013 |
| WO | 2013/019828 | 2/2013 |
| WO | 2015/073481 | 5/2015 |

OTHER PUBLICATIONS

International Search Report issued for PCT Application No. PCT/US2010/038988 dated Aug. 20, 2010.
International Search Report issued for PCT Application No. PCT/US2012/045431 dated Feb. 5, 2013.
International Search Report issued for PCT Application No. PCT/US2012/049097 Dated Sep. 25, 2012.
International Search Report issued for PCT Application No. PCT/US2014/065121 Dated Apr. 8, 2015.
Jaeschke, Georg et al., "Highly Enantioselective Ring Opening of Cyclic Meso-Anhydrides to Isopropyl Hemiesters with Ti-TAD-DOLates: An Alternative to Hydrolytic Enzymes?", The Journal of Organic Chemistry, American Chemical Society, US, vol. 63, No. 4, Jan. 1, 1998, pp. 1190-1197.
Khaselev, N. et al., "The Role of the C—C Double Bond in Alcohol Elimination from MH+ Ions of Unsaturated Bicyclic Esters upon Chemical Ionization", Journal of Mass Spectrometry, vol. 30, No. 11, Nov. 1, 1995, pp. 1533-1538.
Narayanan, A. et al., "Developments in antivirals against influenza, smallpox and hemorrhagic fever viruses", Expert Opinion on Investigational Drugs, Ashley Publications Ltd., London, GB, vol. 20, No. 2, Feb. 1, 2011, pp. 239-254.
Nemecek, Conception et al., "Design of Potent IGF1-R Inhibitors Related to Bis-azaindoles", Chemical Biology & Drug Design, vol. 76, No. 2, Aug. 9, 2010, pp. 100-106.

(Continued)

*Primary Examiner* — Deepak Rao
(74) *Attorney, Agent, or Firm* — Honigman Miller Schwartz and Cohn LLP; Andrew N. Weber; Jonathan P. O'Brien

(57) ABSTRACT

The present invention relates to the novel regioselective syntheses of 2,4-disubstituted pyrimidines through sequential nucleophilic aromatic substitutions.

4 Claims, No Drawings

(56) References Cited

OTHER PUBLICATIONS

Van Baelen, Gitte et al., "Synthesis of 5-methyl-5H-pyrrolo[2,3-c]quinoline and 4-methyl-4H-pyrrolo[2,3-c] isoquinoline: two new unnatural D-ring stripped isomers of the cryptolepine series", Arkivoc, Jan. 1, 2009, pp. 174-182.

Xu, Zhengren et al., "Palladium-Catalyzed Indole and Azaindole Synthesis by Direct Annulation of Electron-Poor o-Chloroanilines and o-Chloroaminopyridines with Aldehydes", Synthesis, vol. 2008, No. 24, Dec. 1, 2008, pp. 3981-3987.

* cited by examiner

METHODS OF REGIOSELECTIVE SYNTHESIS OF 2,4-DISUBSTITUTED PYRIMIDINES

CROSS REFERENCE TO RELATED APPLICATION

This application is a divisional of U.S. patent application Ser. No. 14/506,921, filed on Oct. 6, 2014, which claims the benefit of U.S. provisional application Ser. No. 61/887,570, filed on Oct. 7, 2013. Each of these documents is hereby incorporated by reference in its entirety.

FIELD OF THE INVENTION

The present invention relates to the field of chemistry. More importantly, disclosed herein are methods of regioselectively generating 2,4-disubstituted pyrimidines.

BACKGROUND OF THE INVENTION

The pyrimidine scaffold is found in many natural products and also is a key heteroaryl used in many drug discovery projects. Various substituted pyrimidines have been used to synthesize a variety of protein kinase (e.g., JAK, MAP kinase, tyrosine kinases, and VEGF receptor) inhibitors for treatment or prevention of a wide range of diseases such as cancers, inflammatory bowel disease, or ocular neovascular diseases.

The synthesis of 2,4-disubstituted pyrimidines is facilitated, in part, due to the ready availability of reactive building blocks such as 2,4-dichloropyrimidine or 2-chloro-4-pyrimidone. Nucleophilic aromatic substitutions of 2,4-dichloropyrimidine occur preferentially at C-4 position. However, depending on the nucleophile, product mixtures arising from substitution at C-2 as well as C-4 positions are obtained; resulting in the difficult isolation of pure product. One can circumvent the mixture of products by using different starting materials such as 2-methylthio-4-pyrimidines or 4-thioalkyl-2-pyrimidones. However, this synthetic route also suffers from the drawback of an additional intermediate step between nucleophilic substitution reactions.

SUMMARY OF THE INVENTION

The present invention provides a novel method for generating 2,4-disubstituted pyrimidines through sequential nucleophilic aromatic substitution ($S_NAr$) reactions.

The present invention also provides a regioselective aromatic nucleophilic substitution reaction at C-2 position of the pyrimidine ring.

In one aspect, the present invention provides a method of preparing a compound of Formula I:

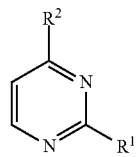

I or pharmaceutically acceptable salt wherein each of $R^1$ and $R^2$ is independently selected from optionally substituted amine, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or optionally substituted fully saturated or partially unsaturated 5-10 membered heterocyclic ring having 1-3 heteroatoms independently selected from N, O, or S; comprising the steps of:
i) reacting a compound of Formula A with a compound of Formula B, wherein $R^3$ is —F, and n is 3-5 to generate a compound of Formula C;

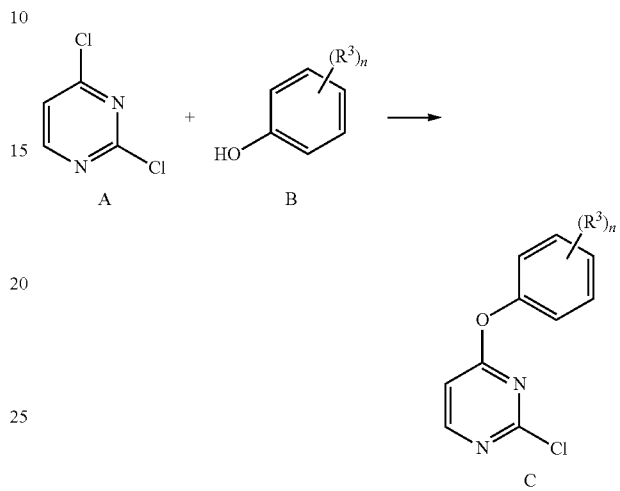

wherein the reaction of step i) is performed in the presence of a base; ii) reacting the compound of Formula C with a $R^1$-reagent to generate a compound of Formula D

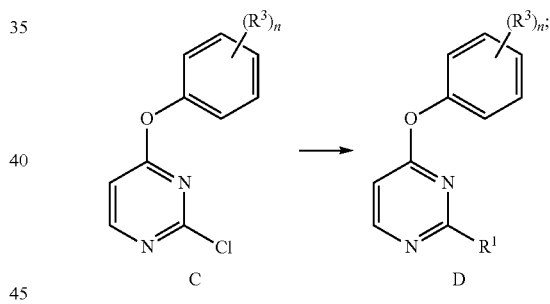

and
iii) reacting the compound of Formula D with a $R^2$-reagent to generate the compound of Formula I.

In some methods, n is 3 or 4. In other methods, n is 4 or 5. And, in some methods, n is 3 or 5. For example, n is 4.

In some methods, the compound of Formula C is selected from

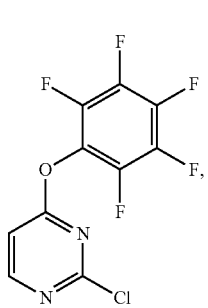

C-1

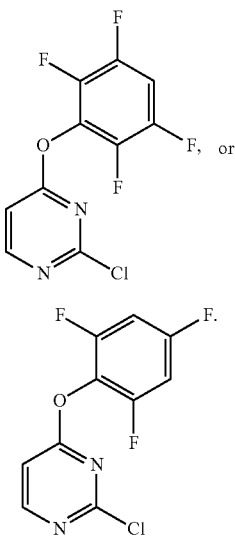

In some methods, the base of step i) is an amine base. For example, the amine base comprises a trialkyl amine, an optionally substituted 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step i) is performed at a temperature of from about room temperature to solvent reflux temperature (e.g., from about 30° C. to about 120° C., from about 50° C. to about 110° C., or from about 70° C. to about 100° C.).

In some methods, $R^1$ is $-NR^{4a}R^{5a}$; the $R^1$-reagent is $HNR^{4a}R^{5a}$; and the reaction of step ii) is performed in the presence of an acid, wherein $R^{4a}$ is —H or $C_{1-4}$ alkyl; and $R^{5a}$ is a mono- or bicyclic aryl, or a 6-10 membered mono- or bicyclic heteroaryl, wherein the aryl or heteroaryl group is optionally substituted.

In some methods, the $R^1$-reagent is $HNR^{4a}R^{5a}$, and $HNR^{4a}R^{5a}$ is selected from

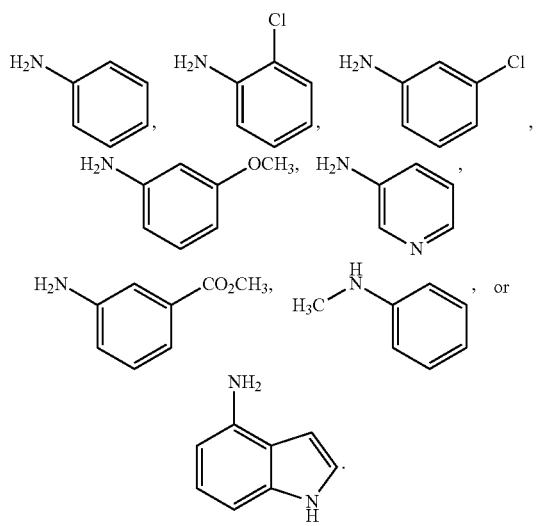

In some methods, the acid of step ii) is selected from TsOH, TFA, AcOH, pivalic acid, a mixture of HCl and EtOH, or any combination thereof. For example, the acid of step ii) is pivalic acid.

In some methods, the reaction of step ii) is performed at a temperature of from about 0° C. to solvent reflux temperature (e.g., from about 0° C. to about 100° C., from about 30° C. to about 90° C., or from about 50° C. to about 70° C.).

In some methods, $R^1$ is $-NR^{4b}R^{5b}$; the $R^1$-reagent is $HNR^{4b}R^{5b}$; and the reaction of step ii) is performed in the presence of a base, wherein $R^{4b}$ is —H or $C_{1-4}$ alkyl; $R^{5b}$ is $C_{1-6}$ alkyl, $C_{3-8}$ cycloalkyl, or a 3-8 membered fully saturated or partially unsaturated heterocyclic ring having 1-3 heteroatoms independently selected from N, O, or S, any of which are optionally substituted with 1-2 groups independently selected from aryl or a 6-10 membered mono- or bicyclic heteroaryl, or $R^{4b}$ and $R^{5b}$ taken together with the nitrogen atom to which they are attached form an optionally substituted 5-8 membered partially saturated or fully saturated heterocyclic ring having up to 1 additional heteroatom selected from N, O, or S.

In some methods, the $R^1$-reagent is $HNR^{4b}R^{5b}$, and $HNR^{4b}R^{5b}$ is selected from

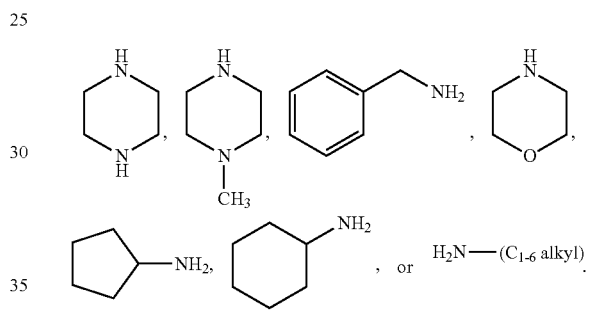

In some methods, the base of step ii) is an amine base. For example, the amine base comprises a trialkyl amine, an optionally substituted 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step ii) is performed at a temperature of from about from about −10° C. to about 75° C. (e.g., from about 0° C. to about 50° C. or from about 15° C. to about 35° C.).

In some methods, $R^1$ is optionally substituted aryl, optionally substituted alkenyl or optionally substituted heteroaryl; the $R^1$-reagent is $(R^6O)_2B-R^1$, wherein each $R^6$ is independently —H, $C_{1-6}$ alkyl, or both ($R^6O$) groups taken together with the boron atom to which they are attached form a 5- or 6-membered heterocyclic ring optionally substituted with 1-4 $C_{1-3}$ alkyl groups; and the reaction of step ii) is performed in the presence of a transition metal catalyst.

In some methods, the transition metal catalyst of step ii) comprises a palladium. For example, the transition metal catalyst of step ii) is a palladium (0) catalyst. In other examples, the transition metal catalyst of step ii) comprises tetrakis(triphenylphosphine) palladium (0).

In some methods, $R^1$ is optionally substituted aryl. For example, $R^1$ is optionally substituted phenyl.

In some methods, $R^1$ is optionally substituted $C_{3-8}$ cycloalkyl, alkenyl, aryl, allyl or optionally substituted fully saturated or partially unsaturated 5-10 membered heterocyclic ring having 1-3 heteroatoms independently selected from N, O, or S; the $R^1$-reagent is X—Zn—$R^1$, wherein X is —Cl, —Br, or —I; and the reaction of step ii) is performed in the presence of a transition metal catalyst.

In some methods, the transition metal catalyst of step ii) comprises nickel or palladium.

In some methods, the transition metal catalyst of step ii) further comprises a triaryl phosphine.

In some methods, $R^1$ is

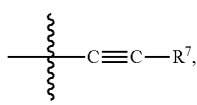

wherein $R^7$ is $C_{1-4}$ alkyl, $C_{2-4}$ alkenyl, $C_{2-4}$ alkynyl, $C_{3-8}$ cycloalkyl, aryl, heteroaryl, or heterocyclyl; the $R^1$-reagent is H—C≡C—$R^7$; and the reaction of step ii) is performed in the presence of a transition metal catalyst.

In some methods, the transition metal catalyst of step ii) comprises copper or palladium.

In some methods, $R^2$ is —$NR^{8a}R^{9a}$; the $R^2$-reagent is $HNR^{8a}R^{9a}$; and the reaction of step iii) is performed in the presence of an acid, wherein $R^{8a}$ is —H or $C_{1-4}$ alkyl; and $R^{9a}$ is a mono- or bicyclic aryl, or a 6-10 membered mono- or bicyclic heteroaryl, wherein the aryl or heteroaryl group is optionally substituted.

In some methods, the $R^2$-reagent is $HNR^{8a}R^{9a}$, and $HNR^{8a}R^{9a}$ is selected from

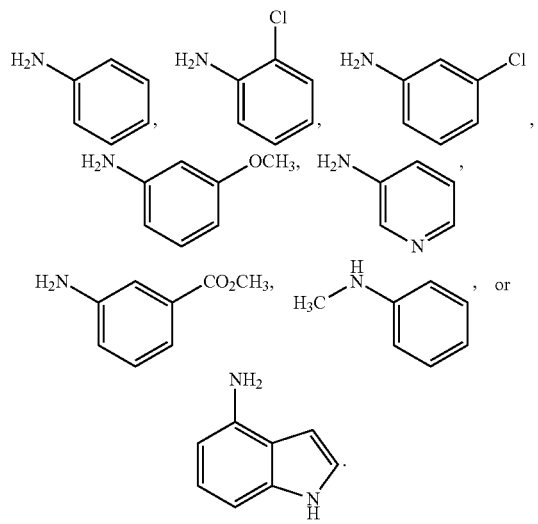

In some methods, the acid of step iii) is a strong acid. In other examples, the acid of step iii) is HBr, $H_2SO_4$, TSOH, pivalic acid, AcOH, HCl, or any combination thereof. In other examples, the acid of step iii) is an inorganic acid. For instance, the acid of step iii) is HCl.

In some methods, the reaction of step iii) is performed at a temperature of from about room temperature to solvent reflux temperature (e.g., from about 40° C. to about 125° C., from about 65° C. to about 115° C., or from about 85° C. to about 105° C.).

In some methods, $R^2$ is —$NR^{8b}R^{9b}$; the $R^2$-reagent is $HNR^{8b}R^{9b}$; and the reaction of step iii) is performed in the presence of a base, wherein $R^{8b}$ is —H or $C_{1-4}$ alkyl; $R^{9b}$ is $C_{1-6}$ alkyl or $C_{3-8}$ cycloalkyl, either of which is optionally substituted with 1-2 groups independently selected from aryl or a 6-10 membered mono- or bicyclic heteroaryl, or $R^{8b}$ and $R^{9b}$ taken together with the nitrogen atom to which they are attached form an optionally substituted 5-8 membered partially saturated or fully saturated heterocyclic ring having up to 1 additional heteroatom selected from N, O, or S.

In some methods, the $R^2$-reagent is $HNR^{8b}R^{9b}$, and $HNR^{8b}R^{9b}$ is selected from

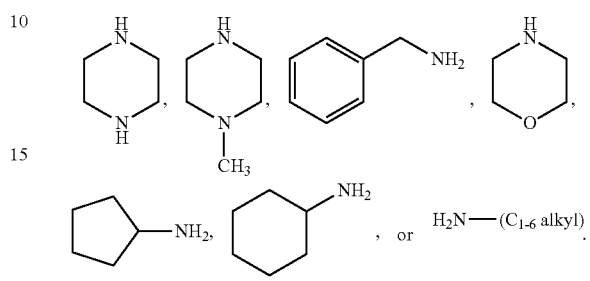

In some methods, the base of step iii) is an amine base. For example, the amine base comprises a trialkyl amine, an optionally substituted 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step iii) is performed at a temperature of from about room temperature to solvent reflux temperature (e.g., from about 60° C. to about 150° C., from about 80° C. to about 130° C., or from about 100° C. to about 120° C.).

Another aspect of the present invention provides a method of preparing a compound of Formula II:

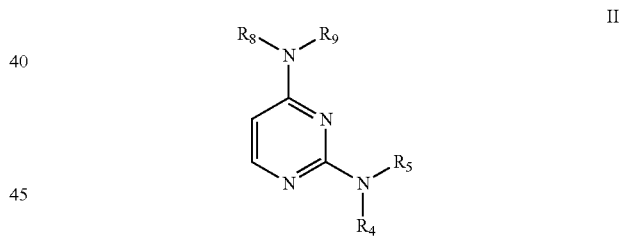

II or pharmaceutically acceptable salt thereof wherein each of $R^4$, $R^5$, $R^8$, and $R^9$, is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or optionally substituted fully saturated or partially unsaturated 5-10 membered heterocyclic ring having 1-3 heteroatoms independently selected from N, O, or S; or $R^4$ and $R^5$ taken together with the nitrogen atom to which they are attached form an optionally substituted 3-8 membered heterocyclic ring having up to 1 additional heteroatom selected from N, O, or S; or $R^8$ and $R^9$ taken together with the nitrogen atom to which they are attached form an optionally substituted 3-8 membered heterocyclic ring having up to 1 additional heteroatom selected from N, O, or S; comprising the steps of: iia) reacting the compound of Formula C, where $R^3$ is —F, and n is 3-5 (e.g., 4) with $NHR^4R^5$ in the presence of an acid or a base to generate a compound of Formula D-1

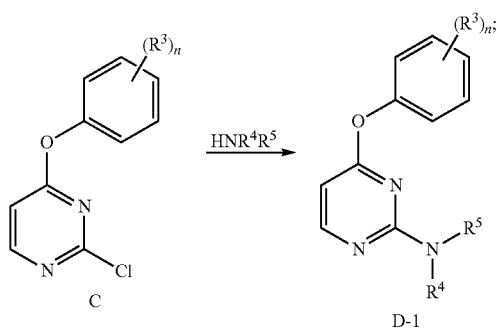

and iiia) reacting the compound of Formula D-1 with NHR⁸R⁹ in the presence of an acid or a base to generate the compound of Formula II.

In some methods, the reaction of step iia) is performed in the presence of an acid; $R^4$ is —H or $C_{1-4}$ alkyl; and $R^5$ is a mono- or bicyclic aryl, or a 6-10 membered mono- or bicyclic heteroaryl, wherein the aryl or heteroaryl group is optionally substituted.

In some methods, HNR⁴R⁵ is selected from

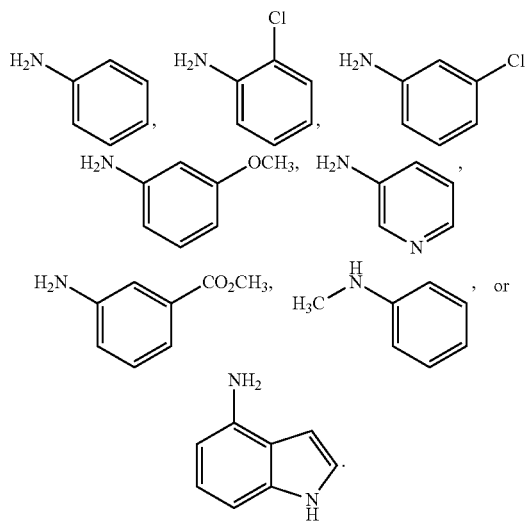

In some methods, the acid of step iia) is selected from TsOH, TFA, AcOH, pivalic acid, a mixture of HCl and EtOH, or any combination thereof. For example, the acid of step iia) is pivalic acid.

In some methods, the reaction of step iia) is performed at a temperature of from about 0° C. to solvent reflux temperature (e.g., from about 0° C. to about 100° C., from about 30° C. to about 90° C., or from about 50° C. to about 70° C.).

In some methods, the reaction of step iia) is performed in the presence of a base; and $R^4$ is —H or $C_{1-4}$ alkyl; $R^5$ is $C_{1-6}$ alkyl or $C_{3-8}$ cycloalkyl, either of which is optionally substituted with 1-2 groups independently selected from aryl or a 6-10 membered mono- or bicyclic heteroaryl, or $R^4$ and $R^5$ taken together with the nitrogen atom to which they are attached form an optionally substituted 5-8 membered partially saturated or fully saturated heterocyclic ring having up to 1 additional heteroatom selected from N, O, or S.

In some methods, HNR⁴R⁵ is selected from

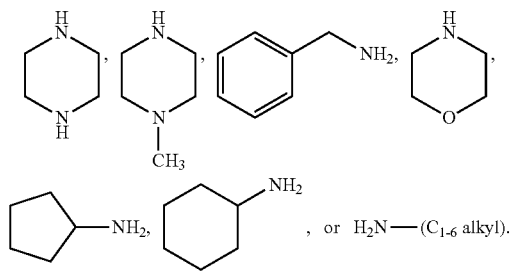

In some methods, the base of step iia) is an amine base. For example, the amine base comprises a trialkyl amine, an optionally substituted 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step iia) is performed at a temperature of from about from about −10° C. to about 75° C. (e.g., from about 0° C. to about 50° C. or from about 15° C. to about 35° C.).

In some methods, the reaction of step iiia) is performed in the presence of an acid; $R^8$ is —H or $C_{1-4}$ alkyl; and $R^9$ is a mono- or bicyclic aryl, or a 6-10 membered mono- or bicyclic heteroaryl, wherein the aryl or heteroaryl group is optionally substituted.

In some methods, HNR⁸R⁹ is selected from

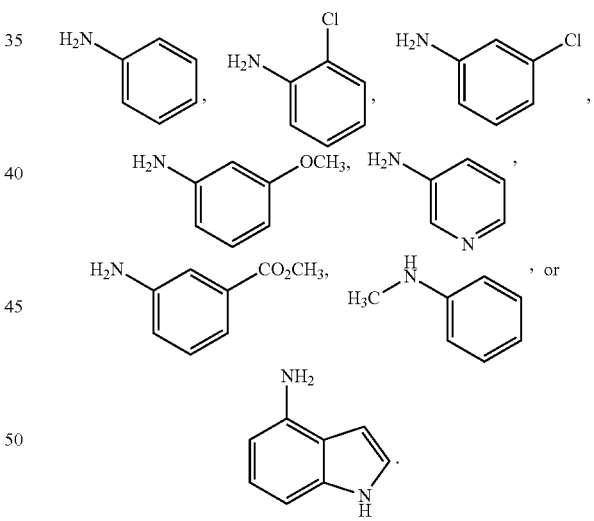

In some methods, the acid of step iiia) is a strong acid. For example, the acid of step iii) is an inorganic acid. In other examples, the acid of step iiia) is HCl.

In some methods, the reaction of step iiia) is performed at a temperature of from about room temperature to solvent reflux temperature (e.g., from about 60° C. to about 150° C., from about 70° C. to about 120° C., or from about 85° C. to about 105° C.).

In some methods, the reaction of step iiia) is performed in the presence of a base; $R^8$ is —H or $C_{1-4}$ alkyl; and $R^9$ is $C_{1-6}$ alkyl or $C_{3-8}$ cycloalkyl, either of which is optionally substituted with 1-2 groups independently selected from aryl or a 6-10 membered mono- or bicyclic heteroaryl, or $R^{8b}$ and $R^{9b}$ taken together with the nitrogen atom to which they are attached form an optionally substituted 5-8 membered partially saturated or fully saturated heterocyclic ring having up to 1 additional heteroatom selected from N, O, or S.

In some methods, $HNR^8R^9$ is selected from

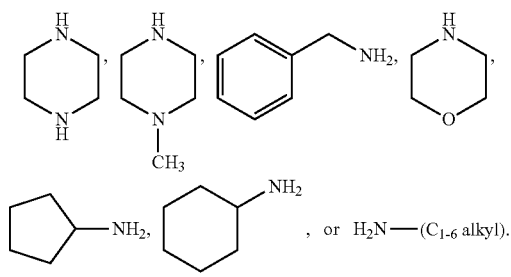

In some methods, the base of step iiia) is an amine base. For example, the amine base comprises a trialkyl amine, an optionally substituted 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step iiia) is performed at a temperature of from about 100° C. to about 120° C.

Some methods further comprise step i): reacting a compound of Formula A with a compound of Formula B to generate the compound of Formula C;

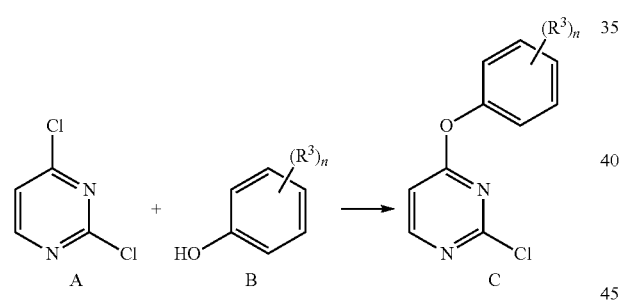

wherein the reaction of step i) is performed in the presence of a base.

In some methods, n is 3 or 5. In other methods, n is 4 or 5. And, in some methods, n is 3 or 5.

In some methods, the compound of Formula C is selected from

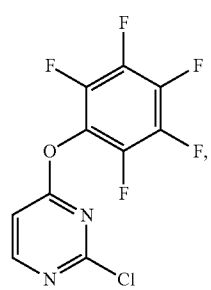

C-1

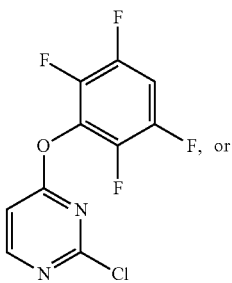

C-2

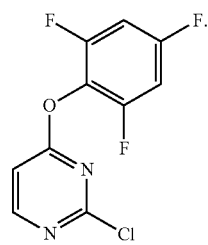

C-3

In some methods, the base of step i) is an amine base such as any of the amine bases described above.

In some methods, the reaction of step i) is performed at a temperature of from about 70° C. to about 100° C.

Another aspect of the present invention provides a compound of Formulae C-1a, C-2a, or C-3a:

C-1a

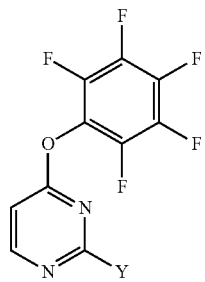

C-2a

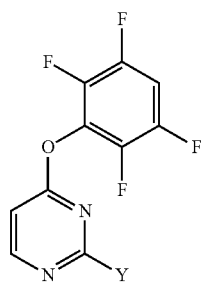

C-3a or pharmaceutically acceptable salt thereof wherein Y is halogen or $-NR^4R^5$; each of $R^4$ and $R^5$, is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or an optionally substituted fully saturated or partially unsaturated 5-10 membered heterocyclic ring having 1-3 heteroatoms independently selected from N, O, or S; or $R^4$ and $R^5$ taken together with the nitrogen atom to which they are attached form an optionally substituted 3-8 membered heterocyclic ring having up to 1 additional heteroatom selected from N, O, or S.

In some embodiments, Y is —Cl.

In some embodiments, Y is —$NR^4R^5$.

DETAILED DESCRIPTION OF THE INVENTION

The present invention provides a novel method for generating 2,4-disubstituted pyrimidines of Formula I

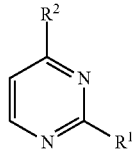

I or pharmaceutically acceptable salts thereof through sequential nucleophilic aromatic substitution ($S_NAr$) reactions, wherein each of $R^1$ and $R^2$ is independently optionally substituted amine, optionally substituted $C_{1-6}$ alkyl, an optionally substituted $C_{2-6}$ alkenyl, an optionally substituted $C_{2-6}$ alkynyl, an optionally substituted aryl, an optionally substituted $C_{3-8}$ cycloalkyl, an optionally substituted heteroaryl, an optionally substituted fully saturated or partially unsaturated 5-10 membered heterocyclic ring having 1-3 heteroatoms independently selected from N, O, or S.

I. Definitions

As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, and alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, a "haloaliphatic" group refers to an aliphatic group substituted with 1-3 halogen atoms on each carbon atom. For instance, the term haloalkyl includes the group —CF$_3$.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ can be aliphatic, cycloaliphatic, aryl, aralphatic, heterocycloaliphatic, heteroaryl or heteroaralphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p, m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic", "alkyl", and "aryl" are defined herein. An example of an araliphatic such as an aralkyl group is benzyl.

As used herein, an "aralkyl" group refers to an alkyl group (e.g., a C$_{1-6}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo

[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl)amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

A "heteroaralipahtic" (such as a heteroaralkyl group) as used herein, refers to an aliphatic group (e.g., a $C_{1-4}$ alkyl group) that is substituted with a heteroaryl group. "Aliphatic", "alkyl", and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

The terms "heterocycle" or "heterocyclic", as used herein indicates a fully saturated, partially saturated, or fully unsaturated 3- to 12-membered monocyclic or bicyclic ring having from 1 to 5 ring heteroatoms selected from O, S, or N. The bicyclic heterocycles may be fused or spirocyclic ring systems. Monocyclic or bicyclic heterocycles, alone, and together with fused or spirocyclic groups, include aziridines, oxirane, azetidine, azirine, thirene, oxetane, oxazetidine, tetrazole, oxadiazole, thiadiazole, triazole, isoxazole, oxazole, oxathiazole, oxadiazolone, isothiazole, thiazole, imidazole, pyrazole, isopyrazole, diazine, oxazine, dioxazine, oxadiazine, thiadiazine, oxathiazole, triazine, thiazine, dithiazine, tetrazine, pentazine, pyrazolidine, pyrrole, pyrrolidine, furan, thiophene, isothiophene, tetrazine, triazine, morpholine, thiazine, piperazine, pyrazine, pyridazine, pyrimidine, piperidine, pyridine, pyran, thiopyran, azepine, diazepine, triazepine, azepane, 3-aza-bicylco[3.2.1]octane, 2-lo aza-bicylco[2.2.1]heptane, octahydrocyclopentapyrrole, aza-bicyclo-nonane, indole, indoline, isoindoline, indolizine, octahydro-isoindole, 2-azaspiro[4.5]decane, 6-azaspiro[2.5]octane, 7-azaspiro[3.5]nonane, 8-azaspiro [4.5]decane, 3-asaspiro[5.5]undecane, 1-oxa-7-azaspiro [4.4]nonane, 1-oxa-8-azaspiro[4.5]decane, purine, benzothiazole, benzoxazole, indazole, benzofuran, and isobenzofuran. Examples of spirocyclic heterocycles include oxaspiro[2.3]hexaneI 1-oxaspiro[3.4]octane, 1-oxaspiro[2.5]octaneI 2-oxaspiro[4.5]decane, 2,6-diazaspiro [3.2]heptane, azaspiro[2.5]octane, 6-aza-spiro[2.5]octane, 1,6-diazaspiro[2.5]octane, 7-aza-spiro[3.5]nonane, 3-azaspiro[5.5]undecane, 8-azaspiro[4.5]decane, 1,3-diazaspiro [4.5]decane, 2,8-diazaspiro[5.5]hendecane, 3,9-diazaspiro [5.5]hendecane, and 1-ox-6-azaspiro[2.5]octane. It will be understood that the terms listed above for heterocycles includes each possible atomic orientation for the groups listed. For instance, the term oxadiazole includes 1,2,3-oxadiazole, 1,3,4-oxadiazole and 1,2,4-oxadiazole; the term thiadiazole includes 1,2,3-thiadiazole, 1,3,4-thiadiazole and 1,2,4-thiadiazole. The term "heterocyclyl" refers to a heterocycle radical.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1] octyl, bicyclo[2.2.2]octyl, bicyclo[3.3.1]nonyl, bicyclo [3.3.2]decyl, 2-oxabicyclo[2.2.2]octyl, 1-azabicyclo[2.2.2] octyl, 3-azabicyclo[3.2.1]octyl, and 2,6-dioxa-tricyclo [3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaralphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$-when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl", which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$— where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted". As described herein, compounds of the invention can optionally be substituted with one or more substituents, such as are illustrated generally above, or as exemplified by particular classes, subclasses, and species of the invention. As described herein, the variables R$^1$-R$^9$ and other variables contained in Formulae I and II described herein encompass specific groups, such as alkyl and aryl. Unless otherwise noted, each of the specific groups for the variables R$^1$-R$^9$ and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted", whether preceded by the term "optionally" or not, refers to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, "chemical purity" refers to the degree to which a substance, i.e., the desired product or intermediate, is undiluted or unmixed with extraneous material such as chemical byproducts.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., tert-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilypethoxylmethyl or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

II. Commonly Used Abbreviations

ACN acetonitrile
tBuOAc tert-butyl acetate
DABCO 1,4-diazabicyclo[2.2.2]octane
DCM dichloromethane
EtOAc ethyl acetate
IPAc iso-propyl acetate
MIBK methyl iso-butyl ketone
TEA triethylamine
THF tetrahydrofuran
PG protecting group
LG leaving group
Ac acetyl
TMS trimethylsilyl
TBS tert-butyldimethylsilyl
TIPS tri-iso-propylsilyl
TBDPS tert-butyldiphenylsilyl
TOM tri-iso-propylsilyloxymethyl
DMP Dess-Martin periodinane
IBX 2-iodoxybenzoic acid
DMF dimethylformamide
MTBE methyl-tert-butylether
TBAF tetra-n-butylammonium fluoride d.e. diastereomeric excess
e.e. enantiomeric excess
DMSO dimethyl sulfoxide
TCA trichloroacetic acid
ATP adenosine triphosphate
EtOH ethanol
Ph phenyl
Me methyl
Et ethyl
Bu butyl
Pr propyl
Pent pentyl
Hex hexyl
DIPEA N,N-diisopropylethylamine
DEAD diethylazodicarboxylate
HEPES 4-(2-hydroxyethyl)-1-piperazineethanesulfonic acid
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time
HOBt hydroxybenzotriazole
Ms mesyl
Ts tosyl
Tf triflyl
Bs besyl
Ns nosyl
Cbz carboxybenzyl
Moz p-methoxybenzyl carbonyl
Boc tert-butyloxycarbonyl
Fmoc 9-fluorenylmethyloxycarbonyl
Bz benzoyl
Bn benzyl
PMB p-methoxybenzyl
DMPM 3,4-dimethoxybenzyl
PMP p-methoxyphenyl
TsOH tosylic acid
AcOH acetic acid
TFA trifluoro acetic acid

III. Methods

In one aspect, the present invention provides a method of preparing a compound of Formula I:

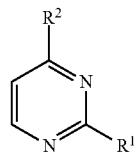

I or pharmaceutically acceptable salt wherein each of $R^1$ and $R^2$ is independently optionally substituted amine, optionally substituted $C_{1-6}$ alkyl, an optionally substituted $C_{2-6}$ alkenyl, an optionally substituted $C_{2-6}$ alkynyl, an optionally substituted aryl, an optionally substituted $C_{3-8}$ cycloalkyl, an optionally substituted heteroaryl, an optionally substituted fully saturated or partially unsaturated 5-10 membered heterocyclic ring having 1-3 heteroatoms independently selected from N, O, or S; comprising the steps of: i) reacting a compound of Formula A with a compound of Formula B, wherein $R^3$ is —F, and n is 3-5 to generate a compound of Formula C

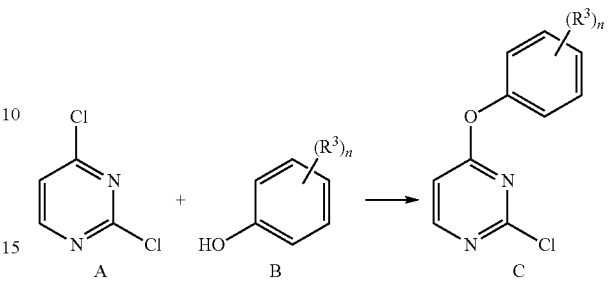

wherein the reaction of step i) is performed in the presence of a base; ii) reacting the compound of Formula C with a $R^1$-reagent to generate a compound of Formula D

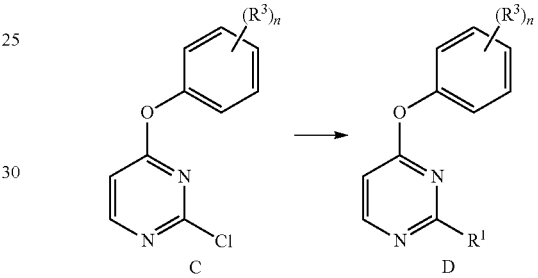

and iii) reacting the compound of Formula D with a $R^2$-reagent to generate the compound of Formula I.

In some methods, n is 3 to 5 (e.g., 4 or 5, or 3 or 5).

In some methods, the compound of Formula C is selected from

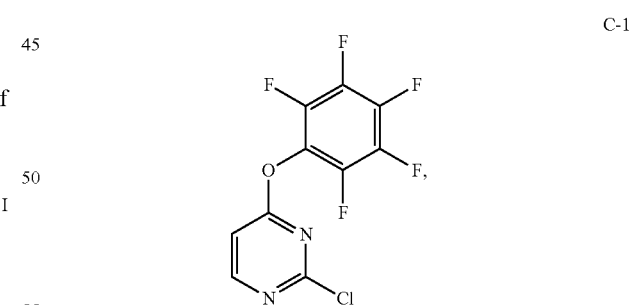

C-1

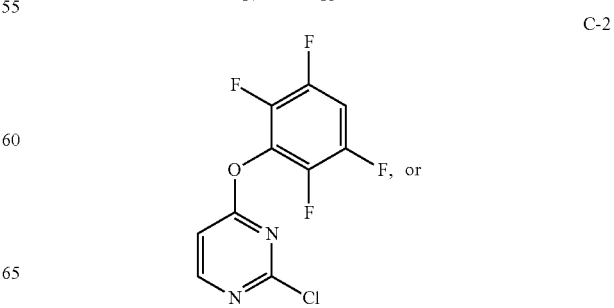

C-2

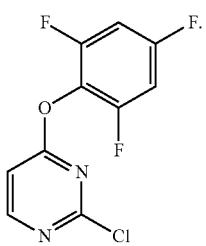

C-3

In some methods, the compound of Formula C is C-2 and in other methods, the compound of Formula C is C-3.

In some methods, the base used in step i) is an amine base. For example, the amine base of step i) comprises a trialkyl amine, an optionally substituted 5-6 membered fully saturated heterocyclic ring having 1-2 nitrogen atoms, or any combination thereof. In other examples, the 5-6 membered fully saturated heterocyclic ring having 1-2 nitrogen atoms is optionally substituted with 1-2 $C_{1-4}$ alkyl groups.

In other examples, the amine base comprises triethylamine, N,N-diisopropylethylamine, pyrrolidine, N-methylpyrrolidine, 1,4-diazabicyclo[2.2.2]octane, or any combination thereof.

In some methods, the reaction of step i) is performed at a temperature of from about room temperature to solvent reflux temperature (e.g., from about 30° C. to about 120° C., from about 50° C. to about 110° C., or from about 70° C. to about 100° C.).

In some methods, the compound of Formula C is converted to a compound of Formula D in step ii) using an $R^1$-reagent, wherein the $R^1$-reagent is $HNR^{4a}R^{5a}$; $R^{4a}$ is —H or $C_{1-4}$ alkyl; and $R^{5a}$ is optionally substituted mono- or bicyclic aryl, or optionally substituted 6-10 membered mono- or bicyclic heteroaryl.

In some of these methods, the reaction of step ii) occurs in the presence of an acid (e.g., pivalic acid). In some methods, the acid of step ii) is selected from TsOH, TFA, AcOH, pivalic acid, a mixture of HCl and EtOH, or any combination thereof. For example, the acid of step ii) is pivalic acid.

In some methods, amines used in step ii) include substituted aromatic amines or heterocyclic amines. In some methods the amines used in step ii) include primary amines or secondary amines. Examples of such amines include:

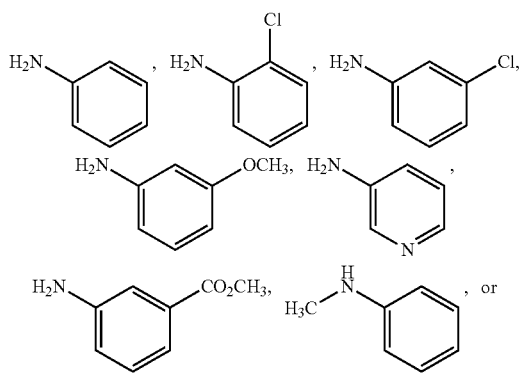

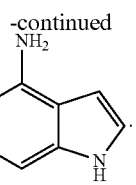

In some methods, the reaction of step ii) is performed at a temperature of from about 0° C. to solvent reflux temperature (e.g., from about 0° C. to about 100° C., from about 30° C. to about 90° C., or from about 50° C. to about 70° C.). In some methods, the reaction of step ii) is performed at temperature of about 60° C.

In some methods, the compound of Formula C is converted to a compound of Formula D in step ii) using an $R^1$-reagent, wherein the $R^1$-reagent is $HNR^{4b}R^{5b}$; $R^{4b}$ is —H or $C_{1-4}$ alkyl; and $R^{5b}$ is $C_{1-6}$ alkyl, $C_{3-8}$ cycloalkyl, or a 3-8 membered heterocyclic ring having 1-3 heteroatoms independently selected from N, O, or S, any of which are optionally substituted with 1-2 groups independently selected from aryl or a 6-10 membered mono- or bicyclic heteroaryl, or $R^{4b}$ and $R^{5b}$ taken together with the nitrogen atom to which they are attached form an optionally substituted 5-8 membered partially saturated or fully saturated heterocyclic ring having up to 1 additional heteroatom selected from N, O, or S. In some of these methods, the reaction of step ii) occurs in the presence of a base.

In some methods, the $R^1$-reagent is $HNR^{4b}R^{5b}$, and $NHR^{4b}R^{5b}$ is selected from

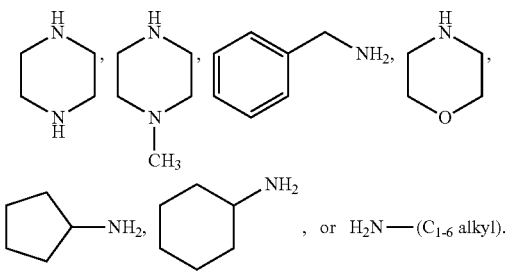

In some methods, the base of step ii) is an amine base.

In some methods, the amine base of step ii) comprises a trialkyl amine, an optionally substituted 5-6 membered fully saturated heterocyclic ring having 1-2 nitrogen atoms, or any combination thereof.

In some methods, wherein the amine base of step ii) comprises triethylamine, N,N-diisopropylethylamine, N-methylpyrrolidine, 1,4-diazabicyclo[2.2.2]octane, or any combination thereof.

In some methods, the reaction of step iia) is performed at a temperature of from about from about −10° C. to about 75° C. (e.g., from about 0° C. to about 50° C. or from about 15° C. to about 35° C.).

In some methods, $R^1$ is optionally substituted aryl or optionally substituted heteroaryl; the $R^1$-reagent is $(R^6O)_2B$—$R^1$, each $R^6$ is independently —H, $C_{1-6}$ alkyl, or both $(R^6O)$ groups taken together with the boron atom to which they are attached form a 5- or 6-membered heterocyclic ring optionally substituted with 1-4 $C_{1-3}$ alkyl groups; and the reaction of step ii) is performed in the presence of a base and transition metal catalyst. In some methods, organotrifluoroborate salts may be used instead of boronic acids. In some methods, the reaction of step ii) is performed under conditions that facilate Suzuku reactions.

In some methods, the transition metal catalyst of step ii) comprises a palladium. For example, the transition metal catalyst of step ii) is a palladium (O) catalyst. In other examples, the transition metal catalyst of step ii) comprises tetrakis(triphenylphosphine) palladium (O).

In some methods, the $R^1$-reagent is $(R^6O)_2B-R^1$ wherein $R^1$ is optionally substituted aryl. For example, the $R^1$-reagent is $(R^6O)_2B-R^1$, and $R^1$ is optionally substituted phenyl.

In some methods, wherein $R^1$ is optionally substituted $C_{3-8}$ cycloalkyl, or optionally substituted fully saturated or partially unsaturated 5-10 membered heterocyclic ring having 1-3 heteroatoms independently selected from N, O, or S; the $R^1$-reagent is $X-Zn-R^1$, X is —Cl, —Br, or —I; and the reaction of step ii) is performed in the presence of a transition metal catalyst. For example, the reaction of step ii) is performed under conditions that facilate Negishi coupling reactions. In some other methods, $R^1$ is optionally substituted $C_{2-8}$ alkenyl, aryl, allyl or $C_{1-6}$ alkyl.

In some methods, the transition metal catalyst of step ii) comprises nickel or palladium.

In some methods, the transition metal catalyst of step ii) further comprises a triaryl phosphine (e.g., triphenyl phosphine).

In some methods, where $R^1$ is

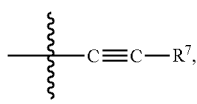

$R^7$ is $C_{2-4}$ alkyl, $C_{2-4}$ alkenyl, $C_{2-4}$ alkynyl, $C_{3-8}$ cycloalkyl, aryl, heteroaryl, or heterocyclyl; the $R^1$-reagent is $H-C\equiv C-R^7$; and the reaction of step ii) is performed in the presence of a transition metal catalyst. In some methods, the reaction occurs under Sonogashira coupling reaction conditions.

In some methods, the transition metal catalyst of step ii) comprises copper or palladium.

In some methods, the compound of Formula D is converted to a compound of Formula I wherein $R^2$ is $-NR^{8a}R^{9a}$; the $R^2$-reagent is $HNR^{8a}R^{9a}$; and the reaction of step iii) is performed in the presence of an acid, wherein $R^{8a}$ is —H or $C_{1-4}$ alkyl; and $R^{9a}$ is a mono- or bicyclic aryl, or a 6-10 membered mono- or bicyclic heteroaryl, wherein the aryl or heteroaryl group is optionally substituted.

In some methods, the $R^2$-reagent is $HNR^{8a}R^{9a}$, and $HNR^{8a}R^{9a}$ is selected from

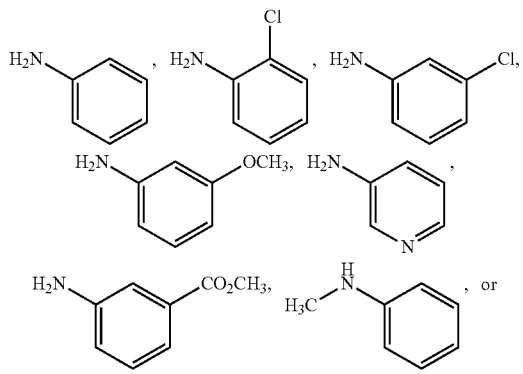

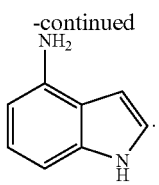

In some methods, the acid of step iii) is a strong acid (e.g., an inorganic acid). For example, the acid of step iii) is HCl or $H_2SO_4$.

In some methods, the reaction of step iii) is performed at a temperature of from about 85° C. to about 105° C. For example, the reaction of step iii) is performed at a temperature of about 95° C.

In some methods, $R^2$ is $-NR^{8b}R^{9b}$; the $R^2$-reagent is $HNR^{8b}R^{9b}$; and the reaction of step iii) is performed in the presence of a base, wherein $R^{8b}$ is —H or $C_{1-4}$ alkyl; $R^{9b}$ is $C_{1-6}$alkyl or $C_{3-8}$ cycloalkyl, either of which is optionally substituted with 1-2 groups independently selected from aryl or a 6-10 membered mono- or bicyclic heteroaryl, or $R^{8b}$ and $R^{9b}$ taken together with the nitrogen atom to which they are attached form an optionally substituted 5-8 membered partially saturated or fully saturated heterocyclic ring having up to 1 additional heteroatom selected from N, O, or S.

In some methods, wherein the $R^2$-reagent is $HNR^{8b}R^{9b}$, and $HNR^{8b}R^{9b}$, is selected from

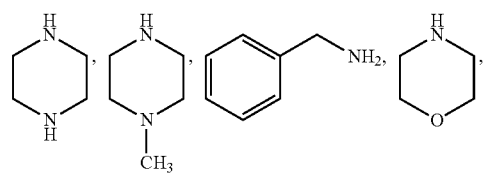

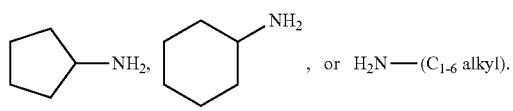

In some methods, wherein the base of step iii) is an amine base.

In some methods, wherein the amine base of step iii) comprises a trialkyl amine, a 5-6 membered fully saturated heterocyclic ring having 1-2 nitrogen atoms, or any combination thereof.

In some methods, the amine base of step iii) comprises triethylamine, N,N-diisopropylethylamine, N-methylpyrrolidine, 1,4-diazabicyclo[2.2.2]octane, or any combination thereof.

In some methods, the reaction of step iii) is performed at a temperature of from about 100° C. to about 120° C. For example, the reaction of step iii) is performed at a temperature at about 110° C.

Another aspect of the present invention provides a method of preparing a compound of Formula II:

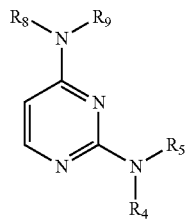

or pharmaceutically acceptable salt thereof, wherein each of $R^4$, $R^5$, $R^8$, and $R^9$ is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or optionally substituted fully saturated or partially unsaturated 5-10 membered heterocyclic ring having 1-3 heteroatoms independently selected from N, O, or S; or $R^4$ and $R^5$ taken together with the nitrogen atom to which they are attached form an optionally substituted 3-8 membered heterocyclic ring having up to 1 additional heteroatom selected from N, O, or S; or $R^8$ and $R^9$ taken together with the nitrogen atom to which they are attached form an optionally substituted 3-8 membered heterocyclic ring having up to 1 additional heteroatom selected from N, O, or S; comprising the steps of: iia) reacting the compound of Formula C, where $R^3$ is —F, and n is 3-5 with $NHR^4R^5$ in the presence of an acid or a base to generate a compound of Formula D-1

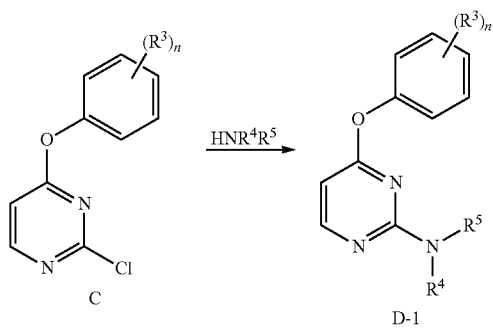

and iiia) reacting the compound of Formula D-1 with $NHR^8R^9$ in the presence of an acid or a base to generate the compound of Formula II.

In some methods, the reaction of step iia) is performed in the presence of an acid wherein $R^4$ is —H or $C_{1-4}$ alkyl; and $R^5$ is an optionally substituted mono- or bicyclic aryl, or an optionally substituted 6-10 membered mono- or bicyclic heteroaryl.

In some methods, $HNR^{4a}R^{5a}$ is selected from

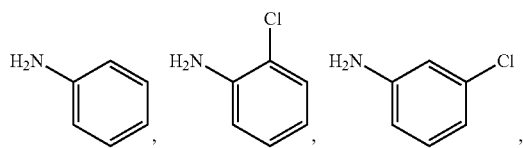

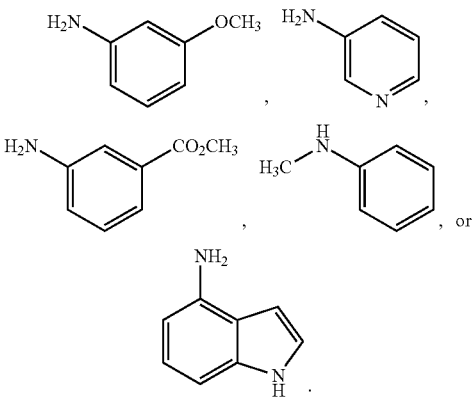

In some methods, the acid of step iia) is pivalic acid.

In some methods, the reaction of step iia) is performed at temperature of from about 50° C. to about 70° C. For example, the reaction of step iia) is performed at temperature of from about 60° C.

In some methods, the reaction of step iia) is performed in the presence of a base; and $R^4$ is —H or $C_{1-4}$ alkyl; and $R^5$ is $C_{1-6}$ alkyl or $C_{3-8}$ cycloalkyl, either of which is optionally substituted with 1-2 groups independently selected from aryl or a 6-10 membered mono- or bicyclic heteroaryl, or $R^4$ and $R^5$ taken together with the nitrogen atom to which they are attached form an optionally substituted 5-8 membered partially saturated or fully saturated heterocyclic ring having up to 1 additional heteroatom selected from N, O, or S.

In some methods, $HNR^4R^5$ is selected from

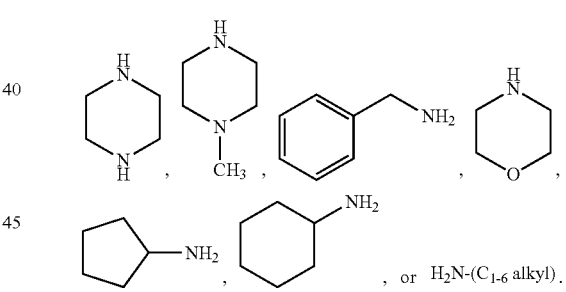

In some methods, the base of step iia) is an amine base. For example, the base of step iia) comprises a trialkyl amine, a 5-6 membered fully saturated heterocyclic ring having 1-2 nitrogen atoms, or any combination thereof. In other examples, the amine base comprises triethylamine, N,N-diisopropylethylamine, N-methylpyrrolidine, 1,4-diazabicyclo[2.2.2]octane, or any combination thereof.

In some methods, the reaction of step iia) is performed at a temperature of from about 15° C. to about 35° C. For example, the reaction of step iia) is performed at a room temperature.

In some methods, the reaction of step iiia) is performed in the presence of an acid; $R^8$ is —H or $C_{1-4}$ alkyl; and $R^9$ is a mono- or bicyclic aryl, or a 6-10 membered mono- or bicyclic heteroaryl, wherein the aryl or heteroaryl group is optionally substituted.

In some methods, HNR⁸R⁹ is selected from

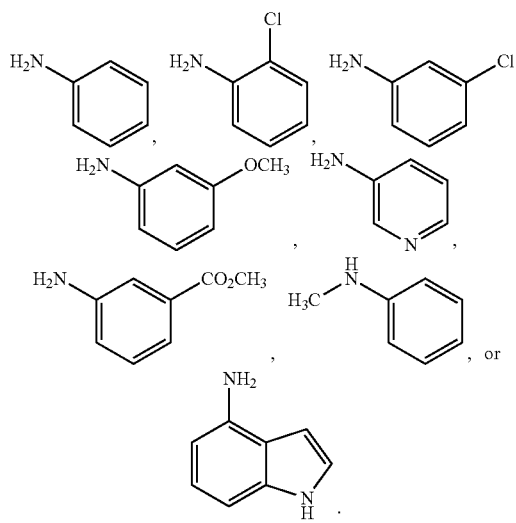

In some methods, the acid of step iiia) is a strong acid (e.g., HCl).

In some methods, the reaction of step iiia) is performed at a temperature of from about 85° C. to about 105° C. For example, the reaction of step iiia) is performed at a temperature of from about 95° C.

In some methods, the reaction of step iiia) is performed in the presence of a base; $R^8$ is —H or $C_{1-4}$ alkyl; and $R^9$ is $C_{1-6}$ alkyl or $C_{3-8}$ cycloalkyl, either of which is optionally substituted with 1-2 groups independently selected from aryl or a 6-10 membered mono- or bicyclic heteroaryl, or $R^{8b}$ and $R^{9b}$ taken together with the nitrogen atom to which they are attached form an optionally substituted 5-8 membered partially saturated or fully saturated heterocyclic ring having up to 1 additional heteroatom selected from N, O, or S.

In some methods, HNR⁸R⁹ is selected from

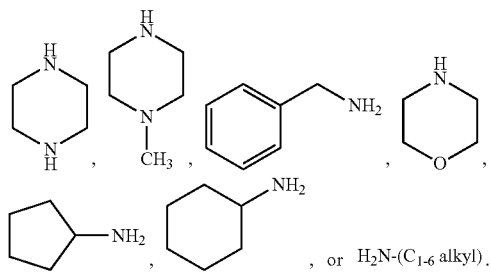

In some methods, the base of step iiia) is an amine base. For example, the base of step iiia) comprises a trialkyl amine, a 5-6 membered fully saturated heterocyclic ring having 1-2 nitrogen atoms, or any combination thereof.

In some methods, wherein the amine base comprises the amine base comprises triethylamine, N,N-diisopropylethylamine, N-methylpyrrolidine, 1,4-diazabicyclo[2.2.2]octane, or any combination thereof.

In some methods, the reaction of step iiia) is performed at a temperature of from about 100° C. to about 120° C. For example, the reaction of step iiia) is performed at a temperature of about 110° C.

In some methods, the preparation of a compound of Formula C comprises step of i): reacting a compound of Formula A with a compound of Formula B:

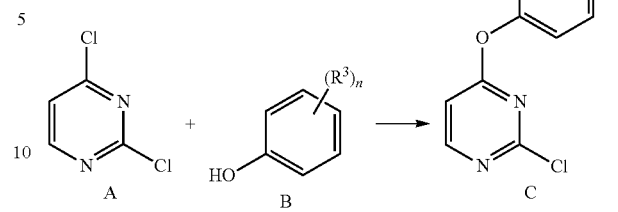

wherein the reaction of step i) is performed in the presence of a base.

In some methods, n is 4 or 5. In some other methods, n is 3 or 4.

In some methods, the compound of Formula C is selected from

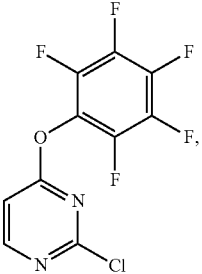

C-1

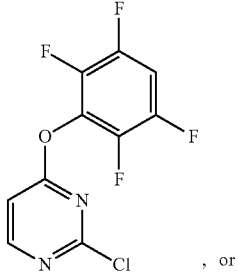

C-2

, or

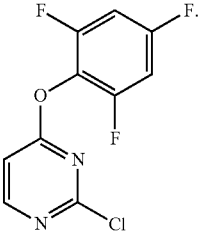

C-3

In some methods, the base of step i) is an amine base such as any of the amine bases described herein. For example, the base of step i) comprises triethylamine, N,N-diisopropylethylamine, piperidine, N-methylpyrrolidine or 1,4-diaza[2.2.2]octane, or any combination thereof.

In some methods, the reaction of step i) is performed at a temperature of from about 70° C. to about 100° C. For example, the reaction of step i) is performed at a temperature of about 80° C.

In some methods, the reaction of step iia) occurs using compound of Formula C and HNR⁴R⁵ wherein $R^4$ is —H or $C_{1-4}$ alkyl; and $R^5$ is a mono- or bicyclic aryl, or a 6-10 membered mono- or bicyclic heteroaryl, wherein the aryl or heteroaryl group is optionally substituted in about 1:1.5 molar ratio.

In some methods, reaction of step iia) occurs using compound of Formula C and HNR⁴R⁵ wherein R⁴ is —H or $C_{1-4}$ alkyl; R⁵ is $C_{1-6}$ alkyl or $C_{3-8}$ cycloalkyl, either of which is optionally substituted with 1-2 groups independently selected from aryl or a 6-10 membered mono- or bicyclic heteroaryl, or R⁴ and R⁵ taken together with the nitrogen atom to which they are attached form an optionally substituted 5-8 membered partially saturated or fully saturated heterocyclic ring having up to 1 additional heteroatom selected from N, O, or S in about 1:1 molar ratio.

In some methods, reaction of step iiia), the reaction occurs using compounds of Formula D-1 and HNR⁸R⁹ wherein R⁸ is —H or $C_{1-4}$ alkyl; and R⁹ is a mono- or bicyclic aryl, or a 6-10 membered mono- or bicyclic heteroaryl, wherein the aryl or heteroaryl group is optionally substituted in about 1 to 1.5 molar ratio.

In some methods, reaction of step iiia), the reaction occurs using compounds of Formula D-1 and HNR⁸R⁹ wherein R⁸ is —H or $C_{1-4}$ alkyl; R⁹ is $C_{1-6}$ alkyl or $C_{3-8}$ cycloalkyl, either of which is optionally substituted with 1-2 groups independently selected from aryl or a 6-10 membered mono- or bicyclic heteroaryl, or R⁴ and R⁵ taken together with the nitrogen atom to which they are attached form an optionally substituted 5-8 membered partially saturated or fully saturated heterocyclic ring having up to 1 additional heteroatom selected from N, O, or S in about 1 to 2 molar ratio.

IV. Compounds

The compounds of the present invention are useful as intermediates in the processes described herein.

Another aspect of the invention provides a compound of Formulae C-1a, C-2a, or C-3a:

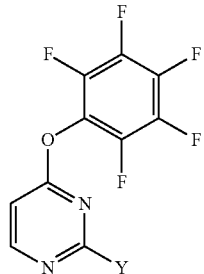

C-1a

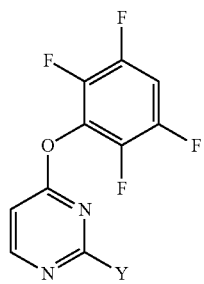

C-2a

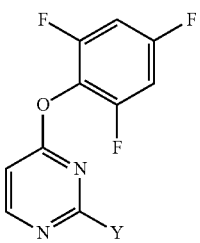

C-3a or pharmaceutically acceptable salt thereof, wherein Y is halogen or —NR⁴R⁵; wherein each of R⁴ and R⁵ is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or optionally substituted fully saturated or partially unsaturated 5-10 membered heterocyclic ring having 1-3 heteroatoms independently selected from N, O, or S; or R⁴ and R⁵ taken together with the nitrogen atom to which they are attached form an optionally substituted 3-8 membered heterocyclic ring having up to 1 additional heteroatom selected from N, O, or S. In some embodiments, Y is —NR⁴R⁵. In other embodiments, Y is halogen (e.g., —Cl, —F, or —Br).

In some embodiments, the invention provides compounds of Formulae C-1, C-2, or C-3:

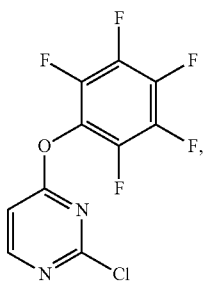

C-1

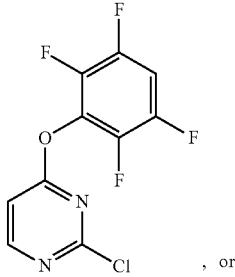

C-2

, or

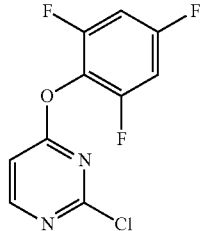

C-3 or pharmaceutically acceptable salts thereof.

In some embodiments, the invention provides a compound of Formulae C-1c, C-2c, or C-3c:

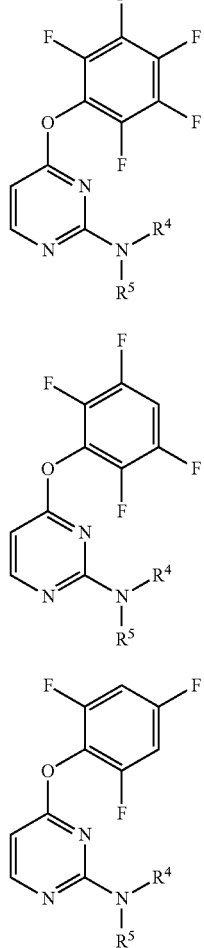

or pharmaceutically acceptable salts thereof, wherein each of $R^4$ and $R^5$, is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or optionally substituted fully saturated or partially unsaturated 5-10 membered heterocyclic ring having 1-3 heteroatoms independently selected from N, O, or S; or $R^4$ and $R^5$ taken together with the nitrogen atom to which they are attached form an optionally substituted 3-8 membered heterocyclic ring having up to 1 additional heteroatom selected from N, O, or S.

V. Synthetic Schemes

The synthetic routes shown and described herein are provided by way of example and are not intended to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1:

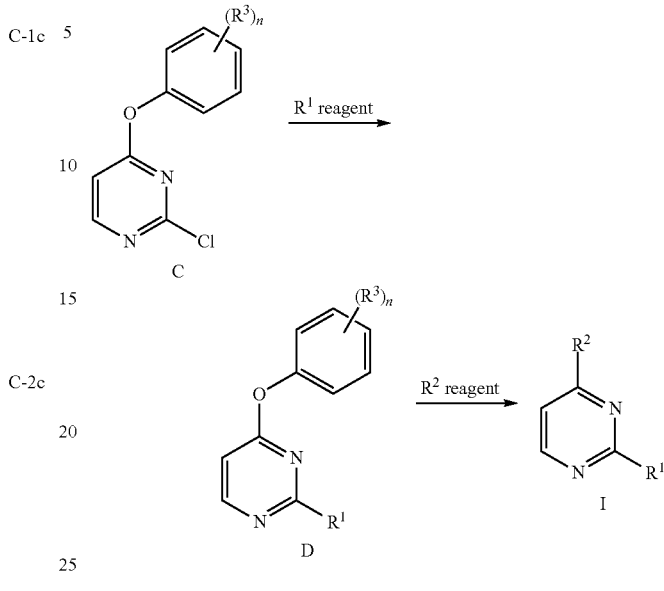

In Scheme 1, compounds of Formula C and D undergo sequential aromatic nucleophilic substitution ($S_NAr$) reactions with $R^1$-reagent and $R^2$-reagent, respectively, in the presence of an acid or a base or a transition metal catalyst to generate the compound of Formula I. The reaction between the compound of Formula C and the $R^1$-reagent can be regioselective.

In Scheme 1, $R^1$-reagent is an aromatic amine or a heterocyclic amine. In some other methods, $R^1$-reagent can be either primary amine or secondary amine. The reaction between the compound of Formula C and aromatic amine can be performed in the presence of an acid and at temperatures from about 50° C. to about 70° C. An examples of a suitable acid is pivalic acid. In some other methods, the reaction between the compound of Formula C and an aliphatic amine can be performed in the presence of a base and at room temperature or about 15° C. to about 35° C. Examples of aliphatic amines include both primary and secondary amines and examples of suitable bases are triethylamine, N,N-diisopropylethylamine, N-methylpyrrolidine, 1,4-diazabicyclo[2.2.2]octane or any combination thereof.

In Scheme 1, $R^1$-reagent is a substituted aryl boronic acid, a substituted heterocyclic boronic acid, or boronic acid ester. In some other methods, $R^1$-reagent is a cycloalkyl or heterocyclic zinc halide. In some other methods, $R^1$-reagent is a substituted terminal alkyne. In some methods, $R^1$-reagent could be any reagent used in Suzuki cross-coupling reactions; any reagent used in Negishi coupling reactions; or any reagent used in Sonogashira coupling reactions. In some methods, the reaction between a compound of Formula C and a boronic acid or ester is conducted in the presence of one or more palladium (0) catalyst. In some other methods, the reaction between a compound of Formula C and an organo zinc halide is conducted in the presence of a nickel or palladium catalyst. In some other methods, the reaction between a compound of Formula C and acetylene is conducted in the presence of a copper or palladium catalyst.

In Scheme 1, C—C bond formation can be achieved when compound of Formula C is engaged in a reaction with various coupling partners and suitable reaction conditions known to those skilled in the art to afford compounds of Formula D. Examples of coupling partners include boronic acids, boronic acid esters, organo zinc halides, acetylinic compounds.

In Scheme 1, R²-reagent is an aromatic amine, heteroaromatic amine, or a heterocyclic amine (e.g., a fully saturated or partially unsaturated heterocycle). In some other methods, R²-reagent can be either primary amine or secondary amine. The reaction between the compound of Formula D and aromatic amine can be performed in the presence of an acid and at temperatures from about 85° C. to about 105° C. Example of suitable acid is hydrochloric acid. In some other methods, the reaction between the compound of Formula D and an aliphatic amine can be performed in the presence of a base and at a temperature of from about 100° C. to about 120° C. Examples of aliphatic amines include both primary and secondary amines and examples of suitable bases are triethylamine, N,N-diisopropylethylamine, N-methylpyrrolidine, 1,4-diazabicyclo[2.2.2]octane or any combination thereof.

Scheme 1A:

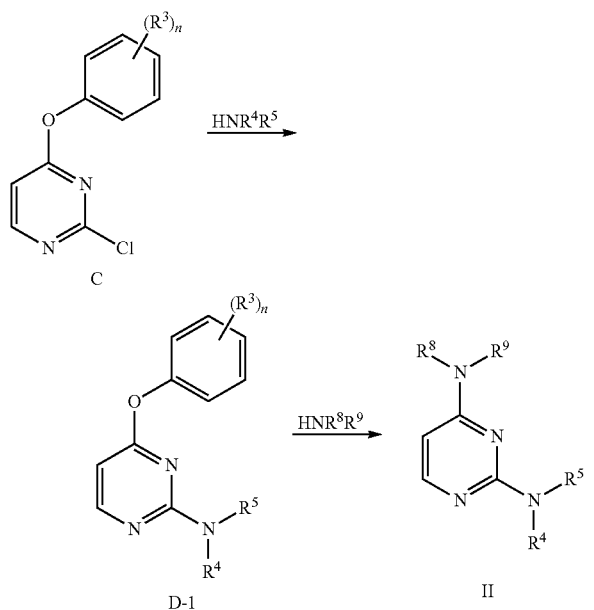

In Scheme 1A, the starting materials that undergo sequential aromatic nucleophilic substitution reactions are compounds of Formulae C and D-1 and nucleophiles are primary or secondary amines in the presence of an acid or base to generate the compound of Formula II. In some methods, the amine is an aliphatic amine, an aromatic amine, a heteroaromatic amine, or a heterocyclic (e.g., a partially saturated for fully saturated heterocycle) amine. In some other methods, amine can be either a primary amine or a secondary amine.

In Scheme 1A, the reaction between the compound of Formula C and aromatic amine can be performed in the presence of an acid and at temperatures from about 50° C. to about 70° C. An examples of a suitable acid is pivalic acid. In some other methods, the reaction between the compound of Formula C and an aliphatic amine can be performed in the presence of a base and at room temperature or about 15° C. to about 35° C. Examples of aliphatic amines include both primary and secondary amines and examples of suitable bases are triethylamine, N,N-diisopropylethylamine, N-methylpyrrolidine, 1,4-diazabicyclo[2.2.2]octane or any combination thereof.

In Scheme 1A, the reaction between the compound of Formula D-1 and aromatic amine, heteroaromatic amine, or heterocyclic amine can be performed in the presence of an acid and at temperatures from about 85° C. to about 105° C. An example of a suitable acid is hydrochloric acid. In some other methods, the reaction between the compound of Formula D-1 and an aliphatic amine can be performed in the presence of a base and at a temperature of from about 100° C. to about 120° C. Examples of aliphatic amines include both primary and secondary amines and examples of suitable bases are triethylamine, N,N-diisopropylethylamine, N-methylpyrrolidine, 1,4-diazabicyclo[2.2.2]octane or any combination thereof.

Scheme 2:

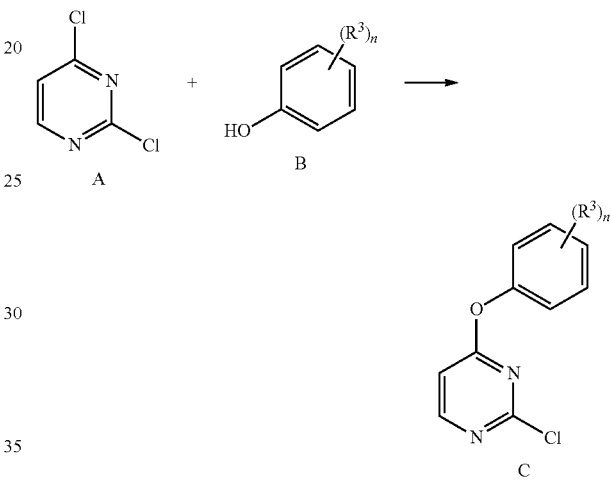

Scheme 2 shows the preparation of compound of Formula C. The compound of Formula A (2,4-dichloropyrimidine) reacts with a compound of Formula B (polyfluoro substituted phenols) under basic conditions to generate compounds of Formula C. Examples of suitable bases include triethylamine, N,N-diisopropylethylamine, N-methylpyrrolidine, 1,4-diazabicyclo[2.2.2]octane, or any combination thereof. The reaction can be performed at temperatures from about 70° C. to about 100° C. In some methods, the reaction can be performed at 80° C.

The methods of the present invention may optionally include additional steps for isolating the final compounds. In some embodiments, the final compounds can be isolated by filtration. In some embodiments, the final compounds can be isolated by triturating with an organic solvent. In some other embodiments, the final compounds can be isolated by triturating with non-polar organic solvents. Examples of solvents include petroleum ether, n-hexanes and diethyl ether. In some embodiments, the final compounds can be purified by chromatography.

VI. Examples

The following preparative examples are set forth in order that this invention is more fully understood. These examples are for the purpose of illustration only and are not to be construed as limiting the scope of the invention in any way.

Example 1

Preparation of Fluorinated 2-chloro-4-phenoxypyrimidines (Compound No. 3)

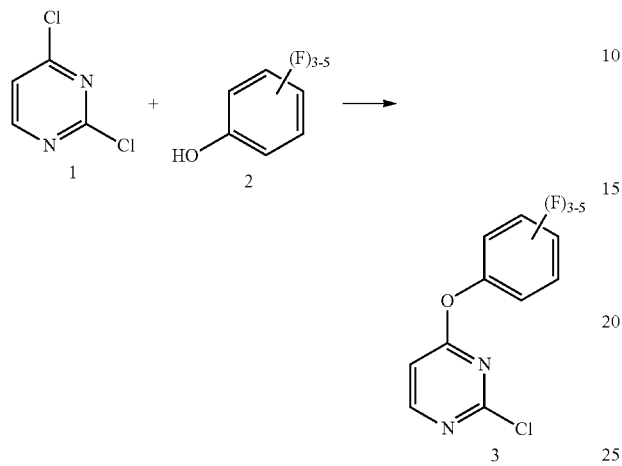

To a solution of 2,4-dichloropyrimidine (compound no. 1, 1 g, 6.71 mmol) in DMF (2 mL) was added the corresponding fluorinated phenol (compound no. 2, 1 eq, 6.71 mmol), followed by diisopropylethyl amine (1.04 g, 1.4 mL, 8.05 mmol) and the mixture was heated to 80° C. for 1 h. The reaction was cooled to ambient temperature and partitioned between a mixture of water and diethyl ether. The organic layer was washed with water two times, aqueous 0.1M sodium hydroxide and brine. The organic layer was then dried over magnesium sulfate, filtered and concentrated in vacuo to yield fluorinated 2-chloro-4-phenoxyprimidines (compound no. 3).

Example 1a

Preparation of Fluorinated 2-chloro-4-(pentafluorophenoxy)pyrimidine (Compound No. C-1)

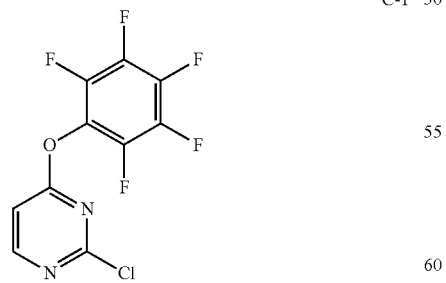

The title compound was prepared according to the general procedure, described in Example 1, using pentafluorophenol in 82% yield (1.63 g). $^1$H NMR (500 Mhz, DMSO-$d_6$) δ 8.61 (d, J=5.7 Hz, 1H), 7.11 (d, J=5.7 Hz, 1H), MS m/z: 296.7 (M+H)$^+$.

Example 1b

Preparation of Fluorinated 2-chloro-4-(2,3,5,6-tetrafluorophenoxy)pyrimidine (Compound No. C-2)

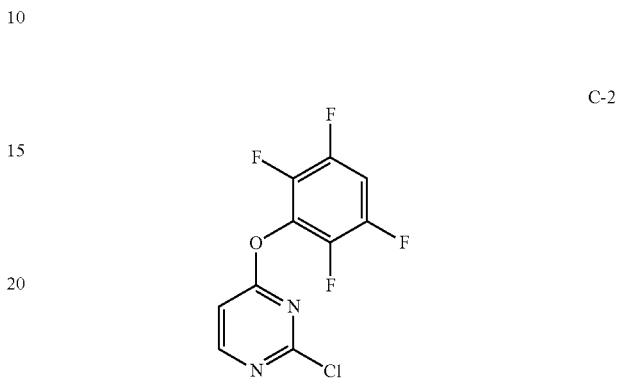

The title compound was prepared according to the general procedure, described in Example 1, using 2,3,5,6-tetrafluorophenol in 84% yield (1.57 g). $^1$H NMR (500 Mhz, DMSO-$d_6$) δ 8.84 (d, J=5.7 Hz, 1H), 8.07-8.0 (m, 1H) 7.61 (d, J=5.7 Hz, 1H), MS m/z: 279.0 (M+H)$^+$.

Example 1c

Preparation of Fluorinated 2-chloro-4-(2,4,6-trifluorophenoxy)pyrimidine (Compound No. C-3)

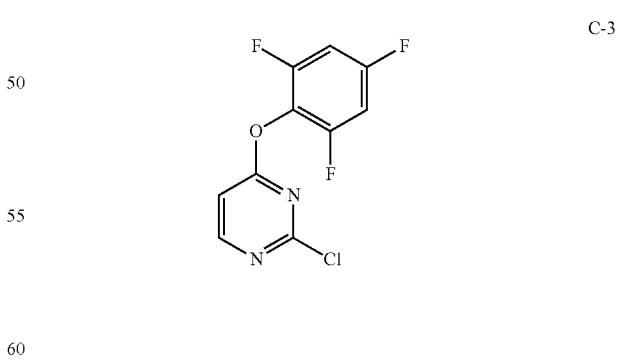

The title compound was prepared according to the general procedure, described in Example 1, using 2,4,6-trifluorophenol in 90% yield (1.57 g). $^1$H NMR (500 Mhz, DMSO-$d_6$) δ 8.56 (d, J=5.7 Hz, 1H), 7.07 (d, J=5.7 Hz, 1H), 6.82-6.88 (m, 2H); MS m/z: 260.0 (M+H)$^+$.

Example 2

Preparation of 2-(N-aryl/heterocyclyl-N—H/alkyl)-4-(2,3,5,6-tetrafluorophenoxy)pyrimidine (Compound No. 4)

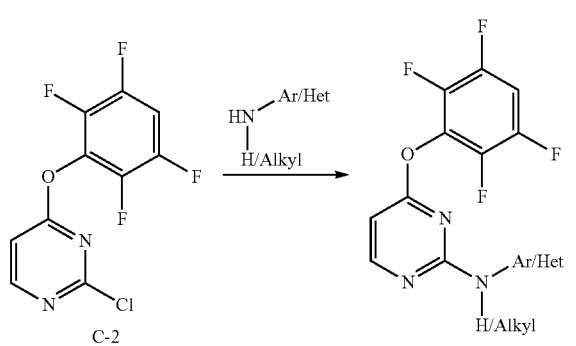

To a mixture of 2-chloro-4-(2,3,5,6-tetrafluorophenoxy)pyrimidine (compound no. C-2, 200 mg, 0.72 mmol) and 2,2-dimethylpropanoic acid (733 mg, 0.412 mL, 7.2 mmol, 10 eq.) was added the aromatic or heterocyclic amine (1.08 mmol, 1.5 eq.) and the mixture was heated to 60° C. for 2 h. The reaction mixture was partitioned between a mixture of water and diethyl ether. The organic layer was washed with water two times, aqueous 0.1M sodium hydroxide and brine. The organic layer was dried over magnesium sulfate, filtered and concentrated in vacuo to yield light yellow solids which were triturated in a small amount of 50/50 diethyl ether/petroleum ether, filtered and dried to yield 2-(N-aryl/heterocyclyl-N—H/alkyl)-4-(2,3,5,6-tetrafluorophenoxy)pyrimidine (compound no. 4) as white solids.

Example 3

Preparation of 2-(N-alkyl-N—H/alkyl)-4-(2,3,5,6-tetrafluorophenoxy)pyrimidine (Compound No. 5)

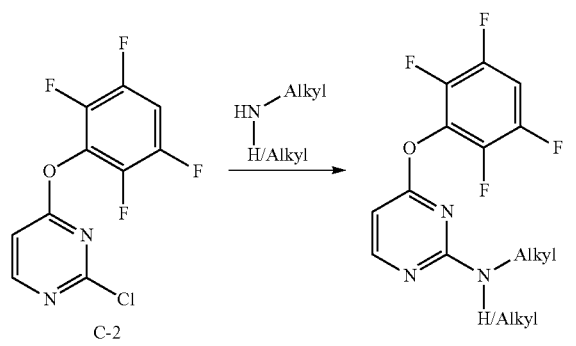

To a solution of 2-chloro-4-(2,3,5,6-tetrafluorophenoxy)pyrimidine (compound no. C-2, 30 mg, 0.11 mmol) in dichloromethane (1 mL) was added the aliphatic amine (0.11 mmol, 1.0 eq.) and triethyl amine (22.2 mg, 30.5 µL, 0.22 mmol, 2 eq.). The mixture was allowed to stir at room temperature for 12 h, before being washed with an aqueous saturated solution of bicarbonate, then brine. The organic layer was dried over magnesium sulfate and concentrated to yield a solid in vacuo. The product was purified by chromatography using a 50/50 diethyl ether/petroleum ether gradient as eluent to yield compounds, 2-(N-alkyl-N—H/alkyl)-4-(2,3,5,6-tetrafluorophenoxy)pyrimidine (compound no. 5), as white solids.

Example 4

Preparation of 2-(N-phenyl)-4-(N-Aryl/Alkyl-N—H/Alkyl)pyrimidine (Compound No. 6a) and 4-(4-N-aryl/heterocyclyl-N—H/alkyl)pyrimidin-2-yl)morpholine (Compound No. 6b)

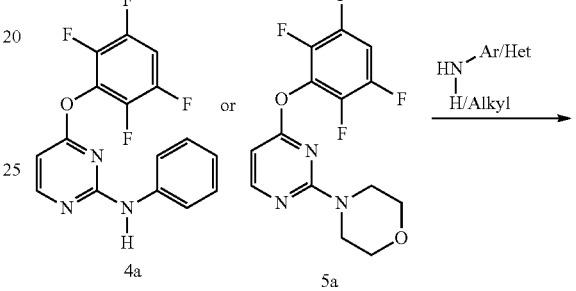

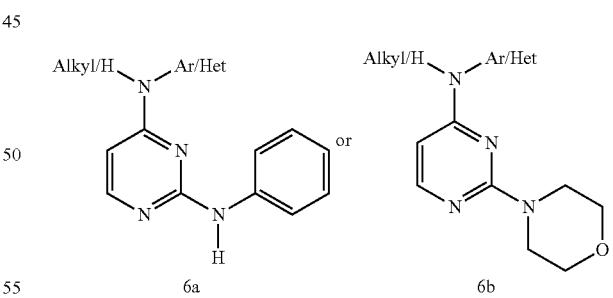

To a solution of N-phenyl-4-(2,3,5,6-tetrafluorophenoxy)pyrimidin-2-amine (compound no. 4a) or 4-(4-(2,3,5,6-tetrafluorophenoxy)pyrimidin-2-yl)morpholine (compound no. 5a) (0.1 mmol) in a mixture of ethanol and water (0.5 mL/0.15 mL) was added the aromatic aniline (0.15 mmol, 1.5 eq.) and a catalytic amount of 2M hydrochloric acid. The mixture was heated 60° C. for 12 h, then cooled to ambient temperature and concentrated to a solid in vacuo. Purification by chromatography using a EtOAc/hexane gradient as eluent provided the title compounds.

Example 5

Preparation of 2-(N-phenyl)-4-(N-Arylalkyl-N—H/Alkyl)pyrimidine (Compound No. 7a) and 4-(4-N-aryl/heterocyclyl-N—H/alkyl)pyrimidin-2-yl)morpholine (Compound No. 7b)

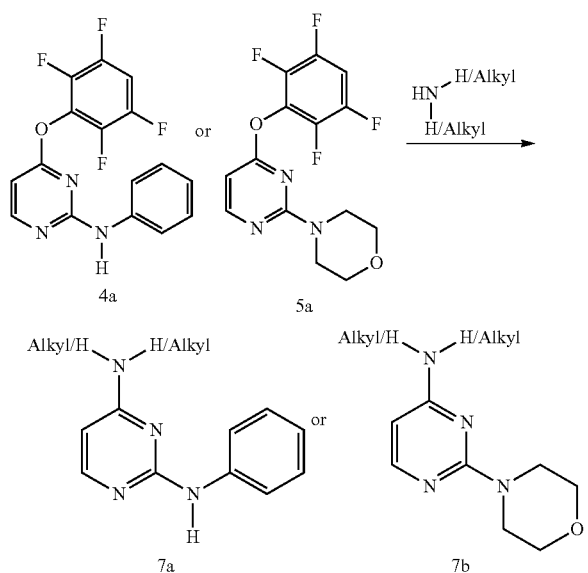

To a solution of N-phenyl-4-(2,3,5,6-tetrafluorophenoxy)pyrimidin-2-amine (compound no. 4a) or 4-(4-(2,3,5,6-tetrafluorophenoxy)pyrimidin-2-yl)morpholine (compound no. 5a) (0.1 mmol) in 0.5 mL of NMP was added the aliphatic amine (0.15 mmol, 1.5 eq.) and diisopropylethyl amine (0.2 mmol, 2 eq.) [in the case of the cyclopentylamine and benzylamine where 3 eq. of the amine and diisopropylethyl amine were used]. The mixture was heated to 110° C. overnight, before being cooled to ambient temperature and concentrated to a solid in vacuo. The residue was purified by chromatography using a EtOAc/hexanes gradient as eluent to provide the title compounds.

Example 6

Regioselectivity Profiles of Aromatic Nucleophilic Substitution Reaction

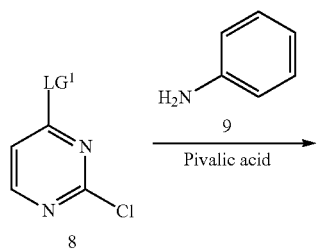

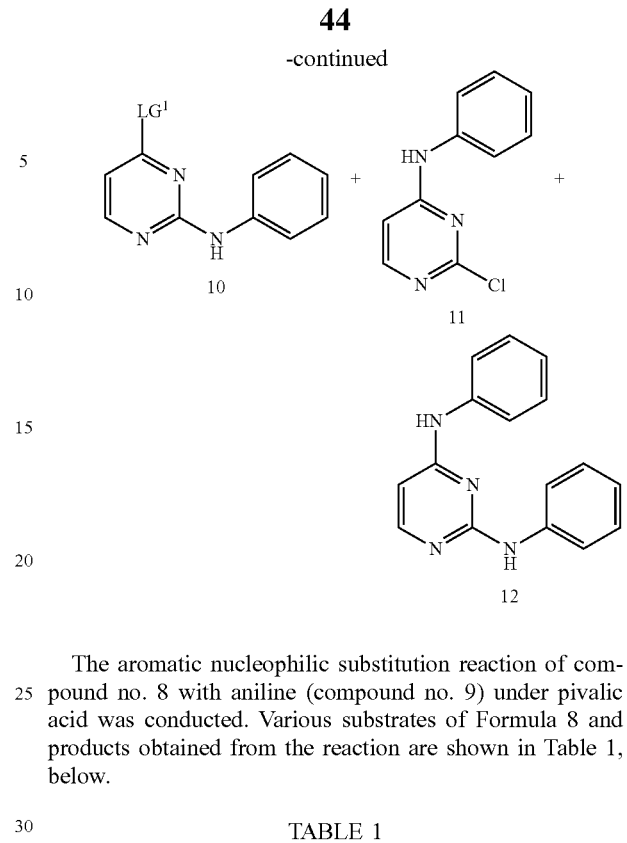

The aromatic nucleophilic substitution reaction of compound no. 8 with aniline (compound no. 9) under pivalic acid was conducted. Various substrates of Formula 8 and products obtained from the reaction are shown in Table 1, below.

TABLE 1

Regioselectivity profiles of aromatic nucleophilic substitution reaction.

| Exp. | Substrate (compound no.) | LG$^1$ | Ratio of 10:11:12 |
|---|---|---|---|
| 6-1 | 1 | Cl | 35:47:18 |
| 6-2 | 3a | Pentafluorophenoxy | 80:8:12 |
| 6-3 | 3b | 2,3,5,6-tetrafluorophenoxy | 93:1:6 |
| 6-4 | 3c | 2,4,6-trifluorophenoxy | 97:1:2 |

The reaction with fluorinated phenoxy substrates (compound no. 3a-3c) resulted higher regioselectivity compared to the substrate, 2,4-dichloropyrimidine (compound no. 1). The nucleophilic substitution reaction occurred at C-2 position in ≥80% with the fluorinated phenoxy substrates. The nucleophilic substitution reaction occurred at C-2 position in ≥90% with the tri- and tetrafluorinated phenoxy substrates (compound nos. 3b and 3c). The highest regioselectivity was achieved with 2-chloro-4-(2,4,6-trifluorophenoxy)pyrimidine substrate (compound no. 3c).

The reactivity of the pentafluorophenoxy substrate, compound no. 3b is the best relative to other substrates. The reactivity of trifluorophenoxy substrate, compound no. 3c, is low compared to tetrafluorophenoxy substrate, 3c in this aromatic nucleophilic substitution reaction.

Example 7

First Aromatic Nucleophilic Substitution Reaction with Aromatic and Heterocyclic Amines Aromatic nucleophilic substitution reactions of compound 3b with aromatic and heterocyclic amines were performed using procedure discussed in Example 2 and the amines used and the yields obtained are specified below in Table 2.

TABLE 2

Aromatic nucleophilic substitution reaction of compound 3b with amines.

| Example | Amine | Isolated yield |
|---|---|---|
| 7-1 | aniline (PhNH₂) | 83 |
| 7-2 | 3-chloroaniline | 74 |
| 7-3 | 3-methoxyaniline | 90 |
| 7-4 | methyl 3-aminobenzoate | 89 |
| 7-5 | 5-aminoindole | 73 |
| 7-6 | 2-chloroaniline | 53 |
| 7-7 | N-methylaniline | 76 |
| 7-8 | 3-aminopyridine | 77 |

Example 8

First Aromatic Nucleophilic Substitution Reaction with Aliphatic Amines

Aromatic nucleophilic substitution reactions of compound 3b with aliphatic amines were performed using procedure discussed in Example 3 and the amines used and the yields obtained are specified below in Table 3.

TABLE 3

Aromatic nucleophilic substitution reaction of compound 3b with amines.

| Example | Amine | Isolated yield (%) |
|---|---|---|
| 8-1 | piperazine | 76 |
| 8-2 | morpholine | 90 |
| 8-3 | benzylamine | 77 |
| 8-4 | n-propylamine | 87 |
| 8-5 | cyclopentylamine | 85 |

Example 9

Second Aromatic Nucleophilic Substitution Reaction with Aromatic, Heteroaromatic, and Heterocyclic Amines Nucleophilic substitution reactions of substrates (compound 4a or 5a) with aromatic, heteroaromatic, and heterocyclic amines were performed using procedure discussed in Example 4 and the amines used and the yields obtained are specified below in Table 4.

TABLE 4

Aromatic nucleophilic substitution reaction of compound 4a or 5a with amines.

| Example | Substrate | Amine | Isolated yield |
|---|---|---|---|
| 9-1 | 4a | aniline | 84 |
| 9-2 | 5a | aniline | 77 |
| 9-3 | 4a | 3-chloroaniline | 86 |
| 9-4 | 5a | 3-chloroaniline | 81 |
| 9-5 | 4a | 3-methoxyaniline | 83 |
| 9-6 | 5a | 3-methoxyaniline | 83 |
| 9-7 | 4a | methyl 3-aminobenzoate | 84 |
| 9-8 | 5a | methyl 3-aminobenzoate | 85 |
| 9-9 | 4a | 5-aminoindole | 86 |
| 9-10 | 5a | 5-aminoindole | 95 |
| 9-11 | 4a | 2-chloroaniline | 43 |
| 9-12 | 5a | 2-chloroaniline | 84 |

TABLE 4-continued

Aromatic nucleophilic substitution reaction of compound 4a or 5a with amines.

| Example | Substrate | Amine | Isolated yield |
|---|---|---|---|
| 9-13 | 4a | (N-methylaniline) | 70 |
| 9-14 | 5a | | 62 |
| 9-15 | 4a | (3-aminopyridine) | 50 |
| 9-16 | 5a | | 64 |

Example 10

Second Aromatic Nucleophilic Substitution Reaction with Aliphatic Amines

Aromatic nucleophilic substitution reactions of substrates (compound 4a or 5a) with aliphatic amines were performed using procedure discussed in Example 5 and the amines used and the yields obtained are specified below in Table 4.

TABLE 4

Aromatic nucleophilic substitution reaction of compound 4a or 5a with amines.

| Example | Substrate | Amine | Isolated yield |
|---|---|---|---|
| 10-1 | 4a | piperazine | 89 |
| 10-2 | 5a | | 87 |
| 10-3 | 4a | morpholine | 92 |
| 10-4 | 5a | | 91 |
| 10-5 | 4a | propylamine | 90 |
| 10-6 | 5a | | 86 |
| 10-7 | 4a | cyclopentylamine | 89 |
| 10-8 | 5a | | 92 |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A compound of Formulae C-1a, C-2a, or C-3a:

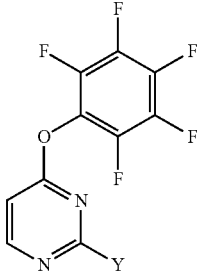

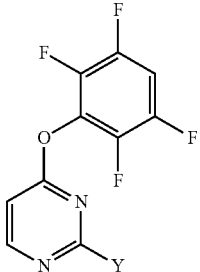

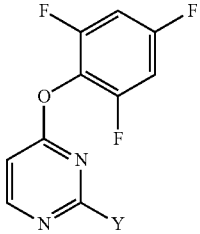

or pharmaceutically acceptable salt thereof, wherein
Y is $-NR^4R^5$; and
each of $R^4$ and $R^5$, is independently —H, optionally substituted $C_{1-6}$ alkyl, optionally substituted $C_{2-6}$ alkenyl, optionally substituted $C_{2-6}$ alkynyl, optionally substituted aryl, optionally substituted $C_{3-8}$ cycloalkyl, optionally substituted heteroaryl, or an optionally substituted fully saturated or partially unsaturated 5-10 membered heterocyclic ring having 1-3 heteroatoms independently selected from N, O, or S; or
$R^4$ and $R^5$ taken together with the nitrogen atom to which they are attached form an optionally substituted 3-8 membered heterocyclic ring having up to 1 additional heteroatom selected from N, O, or S.

2. A compound of Formulae C-1a or C-2a:

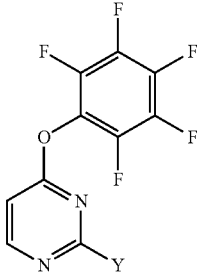

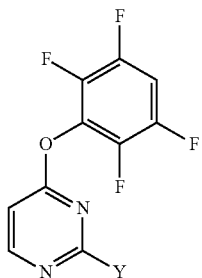

C-2a or pharmaceutically acceptable salt thereof, wherein
Y is halogen or —NR$^4$R$^5$; and
each of R$^4$ and R$^5$, is independently —H, optionally substituted C$_{1-6}$ alkyl, optionally substituted C$_{2-6}$ alkenyl, optionally substituted C$_{2-6}$ alkynyl, optionally substituted aryl, optionally substituted C$_{3-8}$ cycloalkyl, optionally substituted heteroaryl, or an optionally substituted fully saturated or partially unsaturated 5-10 membered heterocyclic ring having 1-3 heteroatoms independently selected from N, O, or S; or
R$^4$ and R$^5$ taken together with the nitrogen atom to which they are attached form an optionally substituted 3-8 membered heterocyclic ring having up to 1 additional heteroatom selected from N, O, or S.

3. The compound of claim 2, wherein Y is —Cl.
4. The compound of claim 2, wherein Y is —NR$^4$R$^5$.

* * * * *